United States Patent [19]

Thomas

[11] Patent Number: 4,963,366

[45] Date of Patent: Oct. 16, 1990

[54] MOLD AND DUST INHIBITING METHOD AND PRODUCT

[76] Inventor: Richard D. Thomas, 812 N. Euclid St., Fullerton, Calif. 92632

[21] Appl. No.: 299,442

[22] Filed: Jan. 23, 1989

Related U.S. Application Data

[60] Continuation-in-part of Ser. No. 606,150, May 2, 1984, Pat. No. 4,806,353, and Ser. No. 166,077, Feb. 26, 1988, Pat. No. 4,847,067, said Ser. No. 606,150, is a continuation-in-part of Ser. No. 536,262, Sep. 27, 1983, abandoned, said Ser. No. 166,077, is a division of Ser. No. 27,878, Mar. 19, 1987, Pat. No. 4,770,878.

[51] Int. Cl.$^5$ .............................................. A01N 59/26
[52] U.S. Cl. .................................. 424/601; 424/608; 424/630; 424/641; 424/646; 424/650; 424/664; 424/670; 424/677; 424/678; 424/672; 514/557; 514/574; 119/1; 426/623
[58] Field of Search ............... 424/601, 608, 630, 641, 424/646, 650, 664, 670, 677, 678, 682; 514/557, 574

[56] References Cited

U.S. PATENT DOCUMENTS

| | | | |
|---|---|---|---|
| 2,816,854 | 12/1957 | Gross | 424/639 |
| 3,404,987 | 10/1968 | Koolstra et al. | 424/639 |
| 4,228,159 | 10/1982 | MacMillan | 424/175 |
| 4,770,878 | 9/1988 | Thomas | 424/141 |
| 4,806,353 | 2/1989 | Thomas | 424/141 |

Primary Examiner—Leonard Schenkman
Attorney, Agent, or Firm—Albert L. Gabriel

[57] ABSTRACT

According to the invention, a liquid deliquescent composition is substantially uniformly applied to grain, animal feed, animal feed ingredients, hay or poultry litter product, inhibiting moisture migration or translocation in the product and thereby inhibiting the formation of mold-generating accumulations of moisture adjacent the walls of storage containers for grain, animal feed, feed ingredients or hay which are subject to large overnight temperature drops, and similary inhibiting the formation of mold-generating accumulations of moisture adjacent the walls of grain elevators or silos subject to large seasonal temperature drops. Such inhibiting of moisture migration or translocation according to the invention also inhibits the formation of dry zones in grain, animal feed, feed ingredients, hay or poultry litter, thereby inhibiting the generation of dust from such products, including the inhibiting of dust generation during the screw-conveying of grain to storage. The inhibiting of moisture migration or translocation in storage containers such as feed bins also inhibits caking and bridging of stored grain, animal feed or feed ingredients proximate the walls and gates of the containers, assuring free exit flow through the gates.

80 Claims, No Drawings

MOLD AND DUST INHIBITING METHOD AND PRODUCT

RELATED APPLICATIONS

The present application is a continuation-in-part of each of two prior pending applications, (1) Ser. No. 606,150, filed May 2, 1984, for MOLD INHIBITING PRODUCT AND METHOD OF MAKING SAME, now U.S. Pat. No. 4,806,353 issued Feb. 21, 1989, and (2) Ser. No. 166,077, filed Feb. 26, 1988, for MOLD AND DUST INHIBITING PRODUCT AND METHOD, now U.S. Pat. No. 4,847,067, issued July 11, 1989.

The first said prior application, Ser. No. 606,150, now U.S. Pat. No. 4,806,353, was a continuation-in-part of Ser. No. 536,262, filed Sept. 27, 1983, now abandoned.

The second said prior application, Ser. No. 166,077, now U.S. Pat. No. 4,847,067, is a divisional of Ser. No. 027,878, filed Mar. 19, 1987, now U.S. Pat. No. 4,770,878, issued Sept. 13, 1988, for MOLD AND DUST INHIBITING PRODUCT AND METHOD.

BACKGROUND OF THE INVENTION

1. Field of the Invention

The present invention is in the field of mold inhibiting products and methods, and also relates to the prevention of harmful dust which is likely to be generated in the handling and use of some products which also characteristically have mold problems, such as grains, animal feeds, animal feed ingredients, and hay.

2. Description of the Prior Art a. Mold Problems

There is a serious worldwide problem of molds growing in food materials, and particularly in grains, animal feeds, animal feed ingredients, and hay. This problem is most serious, and is a year-round problem, in tropical zones of both the eastern and western hemispheres, where sustained high humidities cause excessive moisture to be absorbed in such products, particularly during storage, but also in transit.

This mold problem is also serious in temperate and colder zones on a short-term basis where there are frequent large temperature differentials between night and day, on the order of about 20° F. or more, as occurs in many temperate locations, particularly during the spring and fall seasons; and also on a long-term basis where there are large temperature differentials between the fall harvesting season in which grains are stored and the following winter season during which the storage continues or during other extended periods of storage.

One reason molds present such a serious problem is that they produce dangerous mycotoxins, some of which are carcinogenic. For example, one of the common molds, *Aspergillus Flavus*, produces the mycotoxin aflatoxin which, in addition to other toxic characteristics, interferes with the immune system's ability to produce gamma globulin, the protein that is part of the immune system. The resulting breakdown of the immune system then renders animals that have ingested such mold vulnerable to a variety of diseases.

Mold spores are ubiquitous in the air throughout most of the world, but a primary factor in their ability to propagate on any product is the moisture content of that product. It is well-known in the art that if the moisture content of any product such as grains or feeds is less than approximately 13.5 percent by weight, then the ability of molds to propagate is so seriously limited that mold damage is of little or no concern. However, as the moisture level in the product increases above about 13.5 percent, the vulnerability of the product to mold propagation increases at a surprisingly rapid rate. For example, for applicant's propionate ion-containing mold inhibiting compositions defined in the aforesaid "Related Applications," applicant prescribes the use of three to five pounds per ton of his products for 14 to 16 percent moisture content by weight, 4 to 6 pounds of his product for 16 to 18 percent moisture content by weight, and 5 to 7 pounds of his product for 18 to 20 percent moisture content by weight. Thus, for only about a 4 percent average increase in moisture content, more than a 30 percent increase in the mold inhibiting product is considered by applicant to be desirable for the control of mold propagation.

In view of such sensitivity of molds to the moisture content of products like feeds and grains, the primary means for controlling mold propagation in the art has historically been to limit the moisture content of the products, preferably to not more than approximately 13.5 percent by weight of moisture. Probably the best example of such moisture limitation is the conventional practice for many years of drying grains down to below approximately 13 to 14 percent moisture content by weight in preparation for storage in grain elevators or silos.

However, despite the effectiveness against mold propagation of the procedure of limiting the percentage by weight of moisture in grains or feeds, there are still serious problems to be overcome. For example, where grains are dried down to below approximately 13 to 14 percent moisture content by weight for storage, the feeding quality and efficiency of the grain is impaired when it is so dry, so that it is conventional practice in some areas to add back moisture to the grain after it has been removed from storage to improve its feeding quality and efficiency for cattle. Nevertheless, the feeding quality and efficiency of the grain still remains somewhat diminished by the grain having been subjected to the sucessive steps of drying and remoistening. These steps of drying and remoistening the grain are also disadvantageous because they add materially to the cost of the product.

The most serious problem, whether or not grain, feed or feed ingredients have a moisture content of below about 13 to 14 percent by weight, is that in any bulk storage or transport of grain, feed, or feed ingredients, whether it be grain elevators, silos, tanks, feed bins, railroad tank cars, trucks, barges, ships, or the like, where there develops a substantial temperature differential between relatively warm central regions of the bulk and relatively cold peripheral regions of the bulk, moisture will migrate from the relatively warm central region to the relatively cold peripheral regions, accumulating in the peripheral regions to increase the moisture concentration there, and consequently increase the vulnerability of the products to mold in the peripheral regions. This is true on a short-term basis where the products are stored or transported in tanks, bins, barges or ships at locations where there are large overnight temperature drops, on the order of about 20°-40° F., even with products that have a low moisture content. It is also true on a long-term basis where grains are stored in elevators or silos, being harvested and stored during the fall when temperatures are moderate, and retained in the storage facility through the cold winter months, and sometimes for years. Here, the seasonal temperature differential between inner and outer portions of the grain bulk may be very large, particularly in inland regions such as the plains states of the United States and western Canada.

Referring to the short-term moisture migration problem which occurs in tanks, bins or other containers for grain, feed or feed ingredients where there are large overnight temperature drops, such temperature drops will lower the temperature of the container walls, establishing a large temperature differential between the walls of the container and the temperature of the material within the central region of the container. Water molecules have the characteristic of moving from a warmer zone toward a colder zone, and thus will move or migrate from the central region of the container through the bulk of the material toward the cold walls of the container, increasing the humidity and dampening the material near the walls to provide an excellent growing medium for molds in that region; and this is recognized as a major problem when the humidity level increases to the point where moisture actually condenses on the walls of the container. In many cases, the condensed moisture will drip into the product from the top of the container, and in addition to making it more conducive for mold growth, also serves to deteriorate the quality of the product in other ways. After a few repeated nights of a temperature differential on the order of about 20°-40° F., mold spores which are present all of the time will become active and propagate.

Even with grain, feed or feed ingredients having an average moisture content of 13.5 percent or less, which is conventionally considered to be safe from any substantial mold problem, the moisture content in the material adjacent the container walls will be cumulatively raised higher and higher night after night of such temperature differentials, and a substantial mold problem will develop.

While this may appear to be a localized problem affecting grain, feed or feed ingredients only adjacent container walls, it is likely to grow into a much more extensive problem in the bulk of stored material. It is recognized in the art that even small damp patches of grain or feed in a stored bulk will be likely to initiate development of mold and other adverse growths throughout the bulk of the feed or grain.

This same water migration problem toward cold container walls occurs in connection with the shipping of compressed hay cubes. In the overseas transportation of hay, it is common practice to compress the hay into cubes, and ship such compressed hay cubes in large batches in steel containers. For example, one company of which applicant is aware ships compressed hay cubes in large steel containers. The hay is required to be relatively moist to be compressed into cubes, as for example having a moisture content of approximately 15-16 percent by weight. While such moisture content is not likely to cause a substantial mold problem during the typical 2-3 week voyage if the moisture were to remain substantially uniformly spread throughout the compressed hay, large day/night temperature differentials are frequently encountered during ocean voyages, and in such case, moisture migrates from relatively warm central portions of the containers toward and onto the walls of the containers, greatly increasing the percentage of moisture in the hay adjacent the walls, causing the hay to get moldy in such regions.

The first recognition in the literature of this short-term moisture migration problem in grain of which applicant is aware was a 1969 article by R. W. Disney entitled "The Formation of Dew on a Cooled Surface in Contact With Wheat" (J. stored Prod. Res., 1969, Vol. 5, pp. 281-288. Pergamon Press. Printed in Great Britain). This publication describes a series of tests run by Disney proving the migration of moisture from a warm region in a body of wheat to a relatively cold container wall. Disney theorized in the article that the grain is initially in equilibrium with the intergranular atmosphere but as the container surface is cooled, the relative humidity of the adjacent atmosphere rises and the temperature of the nearby kernels falls, upsetting the equilibrium and causing the kernels near the container surface to absorb water from the air.

Facilities such as grain elevators or silos for the long-term storage of grains which are subject to a large seasonal temperature differential between the fall season when grains are stored and the following winter through which storage continues will have the same moisture migration, or translocation problem, as described in detail above for short-term moisture migration in tanks, bins, or the like. The resulting mold problem in long-term storage facilities can be at least as severe, and sometimes even more severe, than in short-term metal storage containers, because of the extended period of time during which grain may be subjected to generally saturated moisture conditions in zones adjacent walls of the storage facility over the extended storage time and also because of the very large quantities of grain often stored in such facilities. This problem is even more severe where grains are stored for successive years.

Applicant is aware of two early publications which recognize this long-term moisture migration problem, but which do not offer any practical solution. The first of these publications was by Anderson et al. in 1943, entitled "The Effect of Temperature Differential on the Moisture Content of Stored Wheat" (Canadian Journal of Research, Vol. 21, sec. C, pp. 297-306). This publication reports on grain elevator annexes in western Canada each of which held about 30,000 bushels in one pile, the annexes being filled in the fall with sound high-grade wheat of low moisture content, with no ventilation provided above the wheat. In the spring a layer of damp grain 1-2 feet deep had been found to have developed at or near the surface of the grain in a number of the annexes, with moisture contents of 16-18 percent not uncommon. The only cure employed was removal of the damaged grain and fumigation of the remainder when the latter seemed advisable. Prevention methods were crude, including some means of ventilation that could be closed during rain and snow storms, and if the moisture content started to increase near the surface, the grain was shoveled over and thus dried. Long-term experiments were performed on wheat which had a uniform starting moisture content of 14.6 percent. At the end of 316 days, the driest sample taken from the warm zone of the bulk of wheat had a moisture content of 10.9 percent, and the wettest sample taken from the cold zone of the bulk had a moisture content of 29.6 percent.

The second publication of which applicant is aware relating to long-term moisture migration or translocation in bulk stored grain was by T. A. Oxley entitled "The Movement of Heat and Water in Stored Grain" [Am. Ass. Cer. Chem., Transactions 6:84-100 (1948)].

From the last paragraph on page 96 to the top of page 98, Oxley provides an excellent scientific discussion of the mechanism whereby whenever a mass of grain has parts at different temperatures, there is a movement of water from hotter to cooler parts. At page 95, second full paragraph, Oxley indicates the danger of even small damp patches of grain in a bulk of grain, such patches being likely to initiate heating, insect development, and perhaps fungal growth which will spread throughout the bulk; stating that in practice the life of a bulk of grain often is determined by its dampest parts. At page 95, last paragraph, Oxley states that according to frequent observations, some "pockets" of damp grain will certainly persist in otherwise dry bulks for months and even years, and states the common remedy of mixing "tough" with dry grain in order to dry the former which, of course, is a very crude and inconvenient sort of remedy.

A further publication entitled "Diffusion of Moisture Through Grain" by Pixton and Griffiths (J. stored Prod. Res., 1971, Vol. 7, pp. 133-152. Pergamon Press, printed in Great Britain), at page 135 stresses the importance of temperature gradient moisture translocation in grain, as follows: "Translocation of moisture due to temperature gradients is responsible for the mold, caking, sprouting and rotting which occur at the surface of a warm bulk of grain. By itself heating may not damage the grain, but the secondary effects caused by moisture translocation are the main cause of serious damage (Oxley, 1948a). The importance of moisture behavior in the storage, transport and handling of grain cannot be over emphasized. It is one of the most important items in grain technology, the moisture content mainly determining whether the grain will store free from deterioration or not."

b. Dust Problems

In addition to the foregoing mold problems, there are also serious dust problems in connection with the use, handling, and storage of some of these same materials for which there are mold problems as described above.

Dust from animal feeds or feed ingredients is a widespread problem, with a potential for causing lung diseases in various animals, such as horses, cattle, hogs, sheep, and poultry. By way of example, one such dust problem of which applicant is aware that occurs in connection with animal feeds relates to poultry feed. The tips of poultry feed granules have a tendency to dry out and break off from the feed granules, and turn into dust. Such dust when breathed in by the birds can cause serious respiratory diseases such as Aspergillosis.

This same problem occurs with respect to the poultry litter. The litter tends to dry out and generate dust which, when breathed in by the birds, can cause the same diseases as feed dust.

Dust has historically been a serious problem in connection with the storage of grains, as in grain elevators. Dust is generated by screw conveyors conventionally employed to convey grain into elevators, dry surface portions of the grain particles being ground off into dust. This can result in a catastrophic explosive atmosphere in a grain elevator where too much dust is generated and dispersed through the air in the elevator. This problem is compounded where the grain is dried prior to storage down to below 13-14 percent by weight moisture as a mold-inhibiting measure.

c. Bridging and Caking Problems

Another problem in the handling of grain and animal feed is that it tends to cake and "bridge." Moisture from inside the body of grain or feed appears to migrate to a location proximate the walls of the storage bins, including the bin gates. Also, respiration appears to occur in the grain or feed from poor air circulation resulting from such moisture, causing a spontaneous heating and generation of further moisture as a byproduct of the respiration. Accumulation of such moisture causes the caking and bridging to occur, and this produces agglomerations of grain or feed which do not flow freely, and blocks the flow of grain or feed when the gate is opened. This is such a widespread problem that a rubber mallet is placed next to most feed bins in the United States so that the caking and bridging can be shattered by striking the wall of the bin to start the grain or feed flowing.

SUMMARY OF THE INVENTION

In view of these and other problems in the art, it is a general object of the present invention to provide a method and composition for inhibiting the propagation of mold in grain, animal feed, animal feed ingredients and hay.

Another general object of the invention is to provide a method and composition for inhibiting the formation of dust from grain, animal feed, animal feed ingredients and poultry litter.

Another general object of the invention is to provide a method and composition for controlling moisture distribution in the storage or transport of grain, animal feed, feed ingredients or hay.

Another object of the invention is to provide, in the bulk storage or transport of grain, animal feed, feed ingredients or hay materials, a method and composition for inhibiting the migration or translocation of moisture from relatively warm internal zones of the materials to relatively cold peripheral zones of the materials, which would otherwise result from the temperature differential between such relatively warm and relatively cold zones.

Another object of the invention is for the first time to provide a practical solution, in the storage and transport of grain, animal feed, feed ingredients and hay, to the problem of localized moisture accumulation caused by substantial temperature differentials between relatively warm internal zones of the products and relatively cold peripheral zones of the products.

Another object of the invention is for the first time to provide a method and composition for curing the temperature differential moisture migration problem in the bulk storage and transport of grain, animal feed, feed ingredients and hay before such materials are introduced into the storage or transport containers, whereby for the first time the moisture migration problem is prevented before it has a chance to start, rather than after damage may have already been done to the products.

Another object of the invention is to provide a novel mold inhibiting solution which also surprisingly and synergistically has excellent dust inhibiting characteristics, whereby the same solution of the invention when applied to grain, animal feed, feed ingredients, or hay will function to either inhibit the formation and propagation of mold or inhibit the formation of dust.

Another object of the invention is to provide a mold and dust inhibiting solution which, while protecting poultry feed against mold, also protects both poultry feed and poultry litter against the formation of dangerous dust which, when breathed in by the birds, may cause a respiratory disease.

Another object of the invention is to provide a mold and dust inhibiting solution which, when applied to grain, will protect the grain against mold during storage or transport, and will also protect the grain against the production of potentially explosive dust when screw-conveyed into grain elevators or silos for storage.

Another object of the invention is to provide a mold and dust inhibiting method and composition which serve the further function of preventing caking and bridging of grains and animal feeds in metal containers.

A further, more specific object of the invention is to provide a solution containing one or more deliquescent substances which will function both to inhibit the growth of mold and prevent the production of dust with respect to treated products.

A further object of the invention is to provide a solution which will function both to inhibit the growth of mold and to inhibit the production of dust with respect to treated products, which contains as a principal active ingredient at least one deliquescent substance selected from the group consisting of magnesium chloride, calcium chloride, manganese chloride, ferric chloride and zinc chloride.

A further object of the invention is to provide a solution which will function both to inhibit the growth of mold and to inhibit the production of dust with respect to treated products, which contains as a principal active chemical ingredient at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

A further object of the invention is to provide ranges for quantities of deliquescent substance or substances which are effective for the mold and dust inhibiting functions for most conditions of temperature differentials and humidity.

A still further object of the invention is to provide, in the storage and transport of grain, animal feed, feed ingredients and hay, a method and composition which will effectively inhibit the migration or translocation of moisture from relatively warmer internal zones of a body or bulk of grain, feed, feed ingredients or hay to relatively colder peripheral zones proximate container walls, which is equally effective for short-term temperature differentials such as overnight differentials where grain, feed, feed ingredients or hay is stored or transported in metal containers, and for long-term temperature differentials, such as fall/winter seasonal differentials where grain is stored in grain elevators or silos.

Yet a further object of the invention is to provide a composition and method for inhibiting moisture migration or translocation from relatively warmer internal zones of a bulk of grain, feed, feed ingredients or hay to relatively colder peripheral zones, as proximate cold container walls, which is effective to prevent moisture concentrations and consequent mold propagation in the product, regardless of whether the product is relatively dry and is not considered to need an added chemical mold inhibitor such as propionate salt (generally less than approximately 13.5 percent moisture content), or the product is relatively moist (containing more than approximately 13.5 percent moisture), and has an added chemical mold inhibitor.

According to the invention, a solution of one or more deliquescent substances is substantially uniformly applied to grain, animal feed, feed ingredients or hay products prior to storage so as to inhibit the migration or translocation of moisture contained in the treated products from relatively warm internal zones to relatively cold peripheral zones proximate walls of the storage container. By this means, where the treated product is housed for storage or transport in a container subject to large overnight temperature differentials, moisture is inhibited from accumulating adjacent container walls, with consequent inhibiting of mold generation and propagation in the treated products. Similarly, where the treated products are stored in grain elevators or silos, moisture in the products is inhibited from accumulating adjacent walls of the storage facilities despite large seasonal temperature differentials, and mold generation and propagation are thereby inhibited.

By inhibiting moisture migration or translocation, the deliquescent solution of the invention inhibits the formation of dry zones in grain, animal feed, feed ingredients, hay or poultry litter, and thereby inhibits the generation of dust from such products. In the case of both animal feeds and poultry litter, such dust inhibiting by the deliquescent solution of the invention protects the animals from serious respiratory diseases. In the case of grain which is screw-conveyed to storage, the moisture migration inhibiting function of the deliquescent solution of the invention maintains surface moisture in the grain, and thereby inhibits the generation of dust during the screw-conveying, which in turn inhibits the generation of a potentially explosive dust-laden atmosphere in the storage facility.

Further, in metal storage containers such as metal feed bins, the inhibiting of moisture migration or translocation by the deliquescent solution of the invention inhibits caking and bridging of stored animal feed or grain proximate the walls of the containers, including the container gates, and thereby maintains the feed or grain in a free-flowing condition and keeps the container gates clear for the free exit flow of feed or grain through the gates.

The deliquescent material in the solution of the invention may be one or more of a large number of deliquescent substances as set forth hereinafter in the Detailed Description, but is preferably one or more deliquescent substance from the group consisting of magnesium chloride, calcium chloride, manganese chloride, ferric chloride, and zinc chloride.

DETAILED DESCRIPTION

The product of the invention is a mold and dust inhibiting solution which finds particular utility in connection with the storage, transportation and handling of grains, animal feeds, animal feed ingredients and hay, and also in connection with the use of animal litter such as poultry litter. The method of the invention consists of the step or steps employed in applying an effective amount of the solution of the invention to grain, animal feed, animal feed ingredients, hay or poultry litter for inhibiting moisture migration in the product, whereby both mold-propagating accumulations of moisture and dust-propagating dry regions are avoided in the product.

By way of example only, and not of limitation, animal feed ingredients include soy bean meal, peanut meal, cottonseed meal, coconut meal, meat meal, and fish meal.

Mold problems in connection with grains, animal feeds, animal feed ingredients and hay are conventionally thought of as only being present in damp, humid climates. However, applicant has determined that where grains, animal feeds, feed ingredients or hay are stored or transported in bins, tanks, barges, ships or other containers, regardless of the humidity, large short-term temperature variations which are likely to occur between day and night will often cause moisture migration toward and onto the container walls, producing a peripheral concentration of moisture which is conducive to mold propagation.

Similarly, where grains are stored in grain elevators or silos, regardless of the humidity, large long-term temperature variations which occur between the fall season during which grains are normally stored and through the following winter will often cause moisture migration to and onto the walls of such elevators or silos, producing a similar peripheral concentration of moisture which is conducive to mold propagation. Similar large seasonal temperature variations during successive years of storage cumulatively compound this problem.

Dust problems relative to grains, animal feeds, animal feed ingredients, hay and the like are conventionally regarded as dry, low humidity climate problems, and those having ordinary skill in the art would not consider the possibility that a product and method such as the present invention which have particular utility for the control of dampness-propagated mold might also have particular utility for the control of dust. In the present invention, the novel product and method not only effectively control the propagation of mold, but at the same time perform what would normally be considered an opposite function of effectively controlling dust, and the present invention is desirably applied to batches or bulks of grains, feeds, feed ingredients and hay to inhibit and control mold propagation and/or dust production regardless of what environments such batches may be subjected to.

The product of the invention is a solution of deliquescent material. Such deliquescent material is preferably one or more deliquescent substances from the group consisting of magnesium chloride, calcium chloride, manganese chloride, ferric chloride and zinc chloride. While these are the presently preferred deliquescent substances, nevertheless, the deliquescent material may be any one or more deliquescent substances from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

All of these deliquescent materials are edible and hence suitable for application to grain, animal feed and hay intended for human and/or animal consumption. An aqueous solution of the deliquescent material or materials is presently preferred, but it is to be understood that other solutions may be employed.

Applicant's deliquescent solution product provides a plurality of cooperative functions which, at least in part, are unexpected and surprising, and contrary to what those skilled in the art would expect. The strong attraction of the solution of deliquescent material of the invention effectively stops water from evaporating from or coming off any region of the grain, feed, feed ingredients, hay, poultry litter, or other treated product to which the present invention has been applied. This results in the following series of new functions of this invention: (1) On a relatively short-term basis, the deliquescent solution of the present invention bars evaporation of water molecules from relatively warm internal zones in bulks of grain, animal feed, feed ingredients, hay and the like, and migration of such evaporated water molecules toward relatively cold zones such as proximate the walls of storage containers including tanks or bins, transport tanks such as on trucks and railroad cars, barges, ships and the like, under climatic conditions where there is a relatively large temperature differential between day and night, preventing moist, mold-propagating zones from being generated adjacent container walls during storage and transport of such treated materials. (2) Similarly, on a relatively long-term basis, the deliquescent solution of the present invention bars evaporation of water molecules from relatively warm internal zones in bulks of grain stored in grain elevators or silos, and migration of such evaporated water molecules toward relatively cold zones proximate the elevator or silo walls under climatic conditions where there is a relatively large temperature differential between the time of grain storage, usually the fall season when temperatures are moderate, and ensuing very cold winter temperatures, preventing moist, mold-propagating zones from being generated adjacent elevator or silo walls during storage of the treated grain; and the invention will also prevent the formation of such moist zones during successive years of storage where there are large seasonal temperature variation. (3) The deliquescent solution of the invention prevents dry, dust-producing surface zones from developing on grains, feeds, feed ingredients, poultry litter and the like by evaporation of moisture from such surface zones which would occur without the presence of the invention, preventing the production of dust which might be harmful when breathed in by animals, or which might result in calamitous, explosive atmospheres in storage regions such as grain elevators or silos. (4) The deliquescent solution of the invention prevents an increase in localized areas of moisture which might render a mold inhibitor ineffective.

The deliquescent solution of the present invention serves a completely new and unexpected function in the storage of grains, animal feeds and animal feed ingredients which is the opposite of what those skilled in the art would expect the function of a deliquescent substance to be. Deliquescent substances are well known to have a strong attraction for moisture, and for this reason it would be expected that applicant's deliquescent solution would simply draw in moisture from the air trapped in a storage container or elevator or silo each time the cover of the enclosure was opened and then reclosed, and thereby progressively raise the moisture level within the grain, feed or feed ingredient and in due course increase the moisture to a level at which the grain, feed or feed ingredient might be vulnerable to the propagation of mold. However, the presence of applicant's deliquescent solution generally uniformly distributed throughout the grain, feed or feed ingredient has not been found to materially increase the overall moisture content of grain, feed or feed ingredient from air trapped in containers or elevators or silos, even when the covers or other closures of such storage facilities are repeatedly opened and reclosed. It is believed that this is because only a relatively small quantity of applicant's deliquescent solution relative to the quantity of grain, feed or feed ingredient is required for the invention to satisfactorily perform its water anti-migration function, as for example an amount of the deliquescent solution which, when substantially uniformly dispersed throughout the grain, feed or feed ingredient, provides a weight equivalent of approximately 36 to 72 grams of anhydrous deliquescent substance content of the solution per ton of grain, feed or feed ingredient as discussed in detail hereinafter.

The new moisture migration inhibiting function of the deliquescent solution of the invention will be described hereinafter in detail with respect to metal feed bins located in climates where there is a large nighttime temperature drop, on the order of about 20°–40° F., which is the case in many climates, particularly during the spring and fall seasons. It is to be understood that the identical short-term moisture migration inhibiting function of the invention occurs with respect to other containers within which feeds and grains are stored in bulk, such as truck and railroad tank cars, barges, ship containers, ship holds and the like. It is also to be understood that the identical moisture migration inhibiting function of the invention occurs with respect to long-term storage of grains in grain elevators, silos and the like, where a large average seasonal temperature drop occurs, as between fall and winter.

Applying the new moisture migration inhibiting function of applicant's deliquescent solution to products within feed bins, the large overnight drop in temperature of the metal of the bin causes large numbers of water molecules to migrate from the generally warm interior of the mass of feed within the bin toward the cold metal walls of the bin, thereby increasing the dampness of the feed adjacent the walls of the bin. To illustrate this characteristic of water molecules moving from a warmer region toward a cold surface, attention is directed to the fact that considerable amounts of water will almost always condense on the exterior of a glass containing an iced drink, even though the air in that region may seem to be relatively dry.

It is generally recognized in the art that if the moisture content of feed or grain can be kept down to a level of about 13.5 percent or less by weight, there will be no substantial mold problem. However, even if the average moisture content of the feed in a bin is only 13.5 percent, or even less, after a few successive nights during which the overnight temperature drop is on the order of 20°–40° F., cumulative movement of water molecules through the feed from the central region toward the walls of the bin, including the cover wall, will raise the moisture content of the feed near the walls to a much higher percentage than the original 13.5 percent or less average water content, creating a substantial mold problem in the peripheral regions of the bin. When the moisture movement to the walls of the bin reaches the stage where moisture is visibly condensing on the inside of the walls of the bin, then it is recognizable as a major mold problem.

Oxley, in his above-referenced publication "The Movement of Heat and Water in Stored Grain," explains the mechanism of this moisture migration at page 97 of the publication as follows:

"Whenever a mass of grain has parts at different temperatures, there is a movement of water from the hotter to the cooler parts. It is important to know exactly how this occurs. As previously stated, the effect of temperature on the equilibrium relative humidity of grain is comparatively slight so that if a sealed vessel full of grain is hot on one side and cool on the other, the relative humidity of the air remains approximately constant throughout the vessel in spite of the temperature gradient. At any one relative humidity, however, air at a high temperature contains much more water vapor than at a low temperature. Therefore, grain on the hot side of the vessel much [must] give up water vapor to the air, and on the cooled side must absorb some water vapor from the air, in order to maintain constant relative humidity. The temperature gradient in the vessel is therefore matched at first by a corresponding gradient in air-water content. [parenthetical word added]

"Air diffuses continually throughout the vessel. Both by this diffusion and by convection, hot air is continually entering the cool region while cool air enters the hot region. On being cooled, the hot air increases in relative humidity and must therefore give up some water to the surrounding grain in order to restore its humidity to the proper equilibrium value. Conversely, on entering the warm region, cool air absorbs water from the grain. Thus, in the differentially heated vessel, air which diffuses or flows into the cool region gives up water to the grain, while air entering the hot region absorbs water. This continues until the grain in the cool region is so wet, and in the hot region so dry, that a gradient of grain-water content is established."

There is a surprisingly large quantity of water available in feed for such movement of water molecules toward the walls of feed bins, even with a moisture content of the feed down to the 13.5 percent level generally considered safe against mold. Thus, at 13.5 percent moisture content, a 52 lb. bushel of feed contains 7.06 lbs. of water, which is approximately 3.5 quarts. If the 52 lb. bushel contains 16 percent moisture, which is typical for corn that is shipped, then this amounts to 8.32 lbs. of water, or approximately one gallon. To appreciate the tremendous number of water molecules involved in the problem of movement thereof toward the walls of feed bins, 7.06 lbs. of water, the amount in one bushel of feed at 13.5 percent moisture content, according to Avogadro's Number (1) molecular weight of any substance contains 6 times $10^{23}$ molecules), the 7.06 lbs. of water would contain 1.06 times $10^{26}$ water molecules, or 106 trillion trillion molecules of water. It will thus be seen that a very large amount of molecular traffic of water molecules can be caused to occur through a feed bin in response to a large overnight temperature drop.

This water molecule migration through the feed toward the walls of the bin has, surprisingly, been overcome by the deliquescent solution of the invention. The deliquescent solution of the invention is applied so as to be substantially uniformly distributed throughout the body or bulk of feed in the bin, and the deliquescent material has a greater affinity for all of the water molecules throughout the feed than the temperature differential attraction of the cold surfaces of the walls of the bin, so that the water molecules are substantially restrained from the usual and expected movement toward the cold walls of the bin for all temperature fluctuations that would normally be expected. As a result, with the product of the invention generally uniformly distributed throughout the feed, there is no observable increase in the moisture content of the feed adjacent the walls of the bin as compared with the moisture content of the feed throughout the remainder of the bin, regardless of temperature differentials or gradients between central and peripheral regions of the bulk of feed, and consequently there is no increased vulnerability to mold adjacent the walls of the bin.

The above-described moisture anti-migration function of the invention is not only applicable to grains, animal feeds and feed ingredients and hay, but the equally applicable to any material which is protected against mold by having the deliquescent solution of the invention applied thereto. While the invention is applicable to the various types of hay in various storage and transport situation, one example of where the invention is beneficially applicable for mold inhibiting and associated moisture anti-migration in the transport of hay is where hay is shipped by sea in large steel containers. In many shipping areas there is a large day/night temperature differential. This is a particularly severe problem in shipments from the United States to the Orient, where the containers are sometimes on shipboard for 2-3 weeks with hot days and relatively cold nights. While conventionally some materials such as grains are dried as an anti-mold measure, approximately 15-16 percent moisture content is required for compressing the hay cubes, and prior to use of the present invention, there has been a serious mold problem in the shipping of such compacted hay cubes, the moisture from within the containerized batch of cubes migrating toward the container walls because of the day/night temperature differential, thereby increasing the moisture level near the container walls to one which is conducive to mold propagation. While approximately 15-16 percent moisture content is sufficient during such a relatively short period of time for some mold propagation in the hay cubes, it is not sufficient for any serious damage to occur if such percent moisture content were to remain substantially uniformly distributed through the hay cubes. Addition of a chemical mold-inhibiting composition such as propionate salt will be able to completely compensate for this amount of moisture content. However, with large day/night temperature differentials, the percentage moisture content will rise to a much higher level proximate walls of the containers, which could result in a very dangerous mold propagation environment, regardless of an added chemical mold inhibitor such as propionate salt. The deliquescent solution of the present invention solves this problem by controlling the moisture to a substantially uniform distribution of the original stored moisture percentage throughout the bulk of compressed hay in the container.

The deliquescent solution of the present invention, by maintaining substantial moisture uniformity throughout a bulk of grain, feed, feed ingredients or hay, is capable of substantially preventing mold propagation where the average moisture content of the bulk is not substantially greater than about 13.5 percent without the addition of a chemical mold inhibitor additive such as propionate salt covered in applicant's aforesaid applications Ser. Nos. 606,150 and 166,077. Humectant material may also be included in the solution of the present invention as covered in applicant's said applications Ser. Nos. 606,150 and 166,077 without in any way interfering with the efficacy of the deliquescent material in the solution.

The ability of the deliquescent solution of the invention to effectively inhibit the production of dust in connection with the use and handling of grain, feed, feed ingredients, hay and poultry litter is a surprising and synergistic functional addition to the mold inhibiting capability of the invention. The dust inhibiting function of the invention is important in several specific environmental situations of which applicant is aware. There are two separate sources where dust is commonly generated in the production of poultry. First, the tips of poultry feed particles dry and break off into dust, and this is breathed in by the birds and is a common cause of respiratory disease problems such as Aspergillosis. A separate source of dust which is a common cause of these same diseases in birds is poultry litter, which is generally in the form of wood shavings, rice hulls and the like. The litter is periodically rototilled, but nevertheless, areas of the litter commonly dry out and become dusty, and when such dust is breathed in by the birds, it is likely to cause respiratory diseases such as Aspergillosis. When the poultry feed and litter are sprayed with the deliquescent solution of the invention, the deliquescent material causes the moisture to be locked into the product, preventing moisture from evaporating off of surface portions of the feed and litter. The result is that dust will be minimized from the feed or litter.

A very serious dust problem in connection with the handling of grains is the production of relatively large quantities of dust from surface abrasion during the screw conveyor feeding of grains into grain elevators. The potentially catastrophic seriousness of this problem is emphasized by the fact that nine grain elevators blew up from dust explosions in the United States in 1985. This problem is compounded by the fact that grains are conventionally dried before being stored in elevators, the dry surfaces of the grain particles more readily being abraded into dust in screw conveyors. Substantially uniform application of the deliquescent solution of the invention to grain causes moisture to be retained substantially uniformly throughout the grain, including in surface regions of the grain particles, so that surface abrasion and consequent dust production is greatly reduced by application of the invention. Where the grain is dried down to below approximately 13-14 percent by weight of moisture prior to storage according to conventional practice, the deliquescent solution is preferably applied after such drying so that surface portions of the grain have the moisture retaining and hence dust inhibiting characteristics of the invention when the grain is screw-conveyed to storage. Nevertheless, application of the deliquescent solution of the invention to the grain prior to storage generally reduces the necessity for drying of the grain prior to storage by assuring that peripheral zones of grain proximate grain elevator walls will not take on added moisture from warmer, central zones during long-term storage through winter months, whereby substantially uniform and predictable moisture will prevail throughout the bulk of grain during long-term storage.

Another problem which has been surprisingly and unexpectedly solved by the deliquescent solution of the present invention in the storage and handling of grains and animal feeds is what is commonly referred to as the "bridging" of grain of feed. Grain or feed has a tendency to get damp and to cake and bridge in feed bins, producing agglomerations of the grain or feed which are not free-flowing, and tend to block the flow at bin gates. This problem is so universal that most feed bins in the United States have rubber mallets standing beside them which are used to whack the feed bin walls to break up the caking and bridging so as to get the grain or feed flowing through the gate. Associated with this caking and bridging is a spontaneous heating which is sometimes observable in cold weather by steaming of the grain or feed. This is believed to be caused by respiration in the grain or feed involving conversion of soluble carbohydrate to heat and water, which represents a loss in the nutritional value of the grain or feed. Surprisingly, where the grain or feed has been substantially uniformly treated with the deliquescent solution of the invention, such caking and bridging, and spontaneous heating, do not occur, and it is no longer necessary to start the grain or feed flowing at the gate by hitting the bin with a mallet. It is theorized that with the presence of the deliquescent solution of the invention distributed throughout the body of grain or feed in the bin, moisture is not enabled to migrate and thereby accumulate proximate the walls and gate of the bin so as to produce the necessary moisture concentrations for such caking and bridging. It is also theorized that the caking and bridging block ventilation which otherwise would occur through the loose grain or feed, and without air circulation the spontaneous respiration is likely to occur. The moisture generated in the spontaneous respiration or combustion process appears to be an integral part of the caking and bridging process, in that it continuously adds to the moisture present proximate the walls and gate, which in turn tends to make the grain or feed particles stick more and more tightly together as the process proceeds.

The pH of the deliquescent solution of the invention does not appear to be important where a chemical mold inhibiting additive such as propionate salt is not included in the solution. The pH of various deliquescent solutions may vary widely, but applicant has not found this to adversely affect the performance of the invention for various deliquescent substances or combinations thereof. Regardless of the pH, the relatively small weight equivalent of deliquescent substance in the solution of the invention per ton of grain, feed, feed ingredients or hay does not appear to present a corrosion problem where these products are stored in steel containers.

Feed grain such as corn is conventionally rolled with the addition of steam, and if desired, the deliquescent solution of the invention may be applied with the steam. Otherwise, where the solution of the invention is being applied to feed, it preferably may conveniently be applied to the feed at the feed mill, preferably being applied in the mixer when the feed is being mixed. Any application of the solution of the invention can conveniently be made by use of a metering pump, the input end of which is placed in a drum containing the solution of the invention, and the output end leading through a manifold which sprays the solution of the invention onto the grain, feed, feed ingredients, hay or the like. In feeds which contain molasses, a convenient way of applying the solution of the invention is to mix it into the molasses before the molasses is added to the feed.

According to the invention, nonuniform accumulations of moisture in stored grain, animal feed, feed ingredients or hay are inhibited from forming adjacent storage container walls by applying to the grain, animal feed, feed ingredients or hay prior to storage an effective moisture migration inhibiting amount of deliquescent substance or substances. Also, according to the invention, mold and dust generation are inhibited in grain, animal feed, feed ingredients or poultry litter by applying to the grain, animal feed, feed ingredients or poultry litter an effective mold inhibiting and dust generation inhibiting amount of deliquescent substance or substances, such amount comprising an effective moisture migration inhibiting amount of the deliquescent substance or substances. Further, according to the invention, bridging and caking in stored grain, animal feed or feed ingredients are inhibited by applying to the grain, animal feed or feed ingredients prior to storage an effective bridging and caking inhibiting amount of deliquescent substance or substances. Additionally, according to the invention, dust formation is inhibited in the screw-conveying of grain by applying to the grain prior to introduction of the grain into a screw conveyor an effective dust generation inhibiting amount of deliquescent substance or substances.

So so as to not substantially increase the vulnerability of the product grain, feed, feed ingredients, hay, or poultry litter to mold, it is preferred that the amount of the liquid deliquescent composition of the invention be insufficient to cause the grain, feed, feed ingredients, hay, or poultry litter to take on from the air to which it is exposed any substantial amount of additional moisture than it contained upon being treated with the liquid deliquescent composition of the invention.

In the following discussion of weights in grams of deliquescent substance or substances per ton of grain, feed, feed ingredients, hay or poultry litter, and in the corresponding language in the claims, applicant is referring to weight of deliquescent substance or substances in anhydrous form. Similarly, in the following discussion of deliquescent solution strength in terms of percentage by weight of deliquescent substance or substances, and in the corresponding language in the claims, applicant is also referring to weight of deliquescent substance or substances in anhydrous form.

For grain, animal feed, animal feed ingredients, hay, or poultry litter having an average moisture content up to approximately 14 percent, it is preferred that the deliquescent solution of the invention which is substantially uniformly applied to the product contain at least approximately 36 grams of deliquescent substance or substances per ton of the product grain, animal feed, feed ingredients, hay or poultry litter. The amount of deliquescent substance or substances in the solution of the invention should be proportionally increased as the moisture content of the product grain, feed, feed ingredients, hay, or poultry litter increases, up to at least approximately 72 grams of deliquescent substance or substances per ton of the product at approximately 18 percent moisture content in the product grain, feed, hay, or poultry litter. Thus, for approximately 15 percent moisture content in the product, it is preferred to have at least approximately 45 grams of deliquescent substance or substances in the solution of the invention per ton of product to which the invention is applied; for approximately 16 percent product moisture content, it is preferred to provide at least approximately 54 grams of deliquescent substance or substances in the solution of the invention applied per ton of the product; and for approximately 17 percent product moisture content, it is preferred to apply at least approximately 63 grams of deliquescent substance or substances in the solution of the invention applied per ton of the product. It is preferred that not more than approximately 100 grams of deliquescent substance or substances in the solution of the invention be applied per ton of grain, feed, feed ingredients, hay, or poultry litter to avoid any tendency of the deliquescent solution of the invention to attract further moisture into the product.

For most conditions the foregoing ranges are effective. However, it may be desirable to go outside these ranges for extreme conditions of overnight or seasonal temperature differentials or humidity, or for some types and textures of grain, animal feed, feed ingredients, hay or poultry litter.

Referring now to the solution strength of the deliquescent solution of the invention, it is preferred that the solution contain not more than approximately 20 percent by weight of deliquescent substance or substances. With a substantially greater percentage by weight of deliquescent substance or substances in the solution, the solution tends to become difficult to distribute uniformly throughout the grain, feed, hay, or poultry litter.

Applicant has not determined any physical basis for a specific lower limit of the percentage by weight of deliquescent substance or substances to be included in the solution of the invention. However, for a sufficient quantity of deliquescent substance or substances to be applied to grain, animal feed, feed ingredients, hay or poultry litter to substantially prevent moisture migration through the treated product, if the deliquescent solution of the invention were an aqueous solution which was too dilute, an undesirably large amount of moisture would be added to the product, with the possibility of making the product more vulnerable to mold. 0.5 percent by weight of deliquescent substance or substances in the solution of the invention is a presently preferred minimum amount, which appears to provide satisfactory operation of the invention for most circumstances. A presently preferred amount of deliquescent substance or substances in the solution of the invention is approximately 4.0 percent by weight.

While the present invention has been described in what are conceived to be the practical and preferred embodiments, it is recognized that departures may be made therefrom within the scope of the invention, which is therefore not to be limited to the details disclosed herein, but is to be accorded the full scope of the appended claims.

What is claimed is:

1. A method of inhibiting non-uniform accumulations of moisture adjacent wall means of a storage container containing grain, animal feed, animal feed ingredient or hay when said container is subject to large external temperature variations, said method comprising the step of applying to said grain, animal feed, animal feed ingredient or hay prior to introducing said grain, animal feed, animal feed ingredient or hay into said container a propionate free liquid composition comprising an effective moisture migration inhibiting amount of at least one deliquescent substance.

2. A method according to claim 1, wherein said deliquescent substance comprises at least one deliquescent substance from the group consisting of magnesium chloride, calcium chloride, manganese chloride, ferric chloride, and zinc chloride.

3. A method according to claim 1, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

4. A method according to claim 1, wherein said amount of said liquid composition is insufficient to cause said grain, animal feed, feed ingredient or hay to take on from air in said container any substantial amount of additional moisture than it contained when it was introduced into said container.

5. A method according to claim 1, wherein said grain, animal feed, feed ingredient or hay contains, after said application of said liquid composition thereto, at least about 36 grams of said deliquescent substance per ton of said grain, animal feed, feed ingredient or hay.

6. A method according to claim 1, wherein said grain, animal feed, feed ingredient or hay contains, after said application of said liquid composition thereto, not more than about 100 grams of said deliquescent substance per ton of said grain, animal feed, feed ingredient or hay.

7. A method according to claim 1, wherein said grain, animal feed, feed ingredient or hay contains, after said application of said liquid composition thereto, an amount of said deliquescent substance in the range of from about 36 grams to about 72 grams per ton of said grain, animal feed, feed ingredient or hay.

8. A method according to claim 1, wherein said liquid composition contains at least about 0.5 percent by weight of said deliquescent substance.

9. A method according to claim 1, wherein said liquid composition contains not more than about 20 percent by weight of said deliquescent substance.

10. A method according to claim 1, wherein said liquid composition contains an amount of said deliquescent substance in the range of from about 0.5 percent to about 20 percent by weight.

11. A method of inhibiting mold and dust generation in grain, animal feed, animal feed ingredient or hay comprising the step of applying to said grain, animal feed or animal feed ingredient or hay an effective mold inhibiting and dust generation inhibiting amount of a propionate free liquid composition comprising an effective moisture migration inhibiting amount of at least one deliquescent substance.

12. A method according to claim 11, wherein said deliquescent substance comprises at least one deliquescent substance from the group consisting of magnesium chloride, calcium chloride, manganese chloride, ferric chloride, and zinc chloride.

13. A method according to claim 11, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

14. A method according to claim 11, wherein said amount of said liquid composition is insufficient to cause said grain, animal feed, feed ingredient or hay to take on from the air any substantial amount of additional moisture than it contained upon said application of said liquid composition to said grain, animal feed, feed ingredient or hay.

15. A method according to claim 11, wherein said grain, animal feed, feed ingredient or hay contains, after said application of said liquid composition thereto, at least about 36 grams of said deliquescent substance per ton of said grain, animal feed, feed ingredient or hay.

16. A method according to claim 11, wherein said grain, animal feed, feed ingredient or hay contains, after said application of said liquid composition thereto, not more than about 100 grams of said deliquescent substance per ton of said grain, animal feed, feed ingredient or hay.

17. A method according to claim 11, wherein said grain, animal feed, feed ingredient or hay contains, after said application of said liquid composition thereto, an amount of said deliquescent substance in the range of from about 36 grams to about 72 grams per ton of said grain, animal feed, feed ingredient or hay.

18. A method according to claim 11, wherein said liquid composition contains at least about 0.5 percent by weight of said deliquescent substance.

19. A method according to claim 11, wherein said liquid composition contains not more that about 20 percent by weight of said deliquescent substance.

20. A method according to claim 11, wherein said liquid composition contains an amount of said deliquescent substance in the range of from about 0.5 percent to about 20 percent by weight.

21. A method of inhibiting dust generation in a poultry litter composition comprising the step of applying to said poultry litter composition an effective dust generation inhibiting amount of a propionate free liquid composition comprising an effective moisture migration inhibiting amount of at least one deliquescent substance.

22. A method according to claim 21, wherein said deliquescent substance comprises at least one deliquescent substance from the group consisting of magnesium chloride, calcium chloride, manganese chloride, ferric chloride and zinc chloride.

23. A method according to claim 21, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

24. A method according to claim 21, wherein said amount of said liquid composition is insufficient to cause said poultry litter composition to take on from the air any substantial amount of additional moisture than it contained upon said application of said liquid composition to said poultry litter composition.

25. A method according to claim 21, wherein said poultry litter composition contains, after application of said liquid composition thereto, at least about 36 grams of said deliquescent substance per ton of said poultry litter composition.

26. A method according to claim 21, wherein said poultry litter composition contains, after said application of said liquid composition thereto, not more than about 100 grams of said deliquescent substance per ton of said poultry litter composition.

27. A method according to claim 21, wherein said poultry litter composition contains, after said application of said liquid composition thereto, an amount of said deliquescent substance in the range of from about 36 grams to about 72 grams per ton of said poultry litter composition.

28. A method according to claim 21, wherein said liquid composition contains at least about 0.5 percent by weight of said deliquescent substance.

29. A method according to claim 21, wherein said liquid composition contains not more than about 20 percent by weight of said deliquescent substance.

30. A method according to claim 21, wherein said liquid composition contains an amount of said deliquescent substance in the range of from about 0.5 percent to about 20 percent by weight.

31. A method of inhibiting bridging and caking in stored grain, animal feed or animal feed ingredient comprising the step of applying to said grain, feed or feed ingredient prior to storage a propionate free liquid composition comprising an effective bridging and caking inhibiting amount of at least one deliquescent substance.

32. A method according to claim 31, wherein said deliquescent substance comprises at least one deliquescent substance from the group consisting of magnesium chloride, calcium chloride, manganese chloride, ferric chloride and zinc chloride.

33. A method according to claim 31, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

34. A method according to claim 31, wherein said amount of said liquid composition is insufficient to cause said grain, animal feed or feed ingredient to take on from the air any substantial amount of additional moisture than it contained upon said application of said liquid composition to said grain, animal feed or feed ingredient.

35. A method according to claim 31, wherein said grain, animal feed or feed ingredient contains, after said application of said liquid composition thereto, at least about 36 grams of said deliquescent substance per ton of said grain, animal feed or feed ingredient.

36. A method according to claim 31, wherein said grain, animal feed or feed ingredient contains, after said application of said liquid composition thereto, not more than about 100 grams of said deliquescent substance per ton of said grain, animal feed or feed ingredient.

37. A method according to claim 31, wherein said grain, animal feed or feed ingredient contains, after said application of said liquid composition thereto, an amount of said deliquescent substance in the range of from about 36 grams to about 72 grams per ton of said grain, animal feed or feed ingredient.

38. A method according to claim 31, wherein said liquid composition contains at least about 0.5 percent by weight of said deliquescent substance.

39. A method according to claim 31, wherein said liquid composition contains not more than about 20 percent by weight of said deliquescent substance.

40. A method according to claim 31, wherein said liquid composition contains an amount of said deliquescent substance in the range of from about 0.5 percent to about 20 percent by weight.

41. A method of inhibiting dust formation in screw-conveyed grain comprising the step of applying to said grain prior to introduction of the grain into a screw conveyor a propionate free liquid composition comprising an effective dust generation inhibiting amount of at least one deliquescent substance.

42. A method according to claim 41, wherein said deliquescent substance comprises at least one deliquescent substance from the group consisting of magnesium chloride, calcium chloride, manganese chloride, ferric chloride and zinc chloride.

43. A method according to claim 41, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

44. A method according to claim 41, wherein said amount of said liquid composition is insufficient to cause said grain to take on from the air any substantial amount of additional moisture than it contained upon said application of said liquid composition to said grain.

45. A method according to claim 41, wherein said grain contains, after said application of said liquid composition thereto, at least about 36 grams of said deliquescent substance per ton of said grain.

46. A method according to claim 41, wherein said grain contains, after said application of said liquid composition thereto, not more than about 100 grams of said deliquescent substance per ton of said grain.

47. A method according to claim 41, wherein said grain contains, after said application of said liquid composition thereto, an amount of said deliquescent substance in the range of from about 36 grams to about 72 grams per ton of said grain.

48. A method according to claim 41, wherein said liquid composition contains at least about 0.5 percent by weight of said deliquescent substance.

49. A method according to claim 41, wherein said liquid composition contains not more than about 20 percent by weight of said deliquescent substance.

50. A method according to claim 41, wherein said liquid composition contains an amount of said deliquescent substance in the range of from about 0.5 percent to about 20 percent by weight.

51. A grain composition comprising at least one grain and an effective mold inhibiting and dust generation inhibiting amount of a propionate free liquid composition comprising an effective moisture migration inhibiting amount of at least one deliquescent substance.

52. A grain composition according to claim 51, wherein said deliquescent substance comprises at least one deliquescent substance from the group consisting of magnesium chloride, calcium chloride, manganese chloride, ferric chloride and zinc chloride.

53. A grain composition according to claim 51, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

54. A grain composition according to claim 51, wherein said amount of said liquid composition is insufficient to cause said grain to take on from the air any substantial amount of additional moisture than it contained upon application of said liquid composition to said grain.

55. A grain composition according to claim 51, wherein said grain contains at least about 36 grams of said deliquescent substance per ton of said grain.

56. A grain composition according to claim 51, wherein said grain contains not more than about 100 grams of said deliquescent substance per ton of said grain.

57. A grain composition according to claim 51, wherein said grain contains an amount of said deliquescent substance in the range of from about 36 grams to about 72 grams per ton of said grain.

58. A grain composition according to claim 51, wherein said liquid composition contains at least about 0.5 percent by weight of said deliquescent substance.

59. A grain composition according to claim 51, wherein said liquid composition contains not more than about 20 percent by weight of said deliquescent substance.

60. A grain composition according to claim 51, wherein said liquid composition contains an amount of said deliquescent substance in the range of from about 0.5 percent to about 20 percent by weight.

61. An animal feed composition comprising at least one animal feed material and an effective mold inhibiting and dust generation inhibiting amount of a propionate free liquid composition comprising an effective moisture migration inhibiting amount of at least one deliquescent substance.

62. An animal feed composition according to claim 61, wherein said deliquescent substance comprises at least one deliquescent substance from the group consisting of magnesium chloride, calcium chloride, manganese chloride, ferric chloride and zinc chloride.

63. An animal feed composition according to claim 61, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

64. An animal feed composition according to claim 61, wherein said amount of said liquid composition is insufficient to cause said animal feed material to take on from the air any substantial amount of additional moisture than it contained upon application of said liquid composition to said animal feed material.

65. An animal feed composition according to claim 61, wherein said animal feed material contains at least about 36 grams of said deliquescent substance per ton of said animal feed material.

66. An animal feed composition according to claim 61, wherein said animal feed material contains not more than about 100 grams of said deliquescent substance per ton of said animal feed material.

67. An animal feed composition according to claim 61, wherein said animal feed material contains an amount of said deliquescent substance in the range of from about 36 grams to about 72 grams per ton of said animal feed material.

68. An animal feed composition according to claim 61, wherein said liquid composition contains at least about 0.5 percent by weight of said deliquescent substance.

69. An animal feed composition according to claim 61, wherein said liquid composition contains not more than about 20 percent by weight of said deliquescent substance.

70. An animal feed composition according to claim 61, wherein said liquid composition contains an amount of said deliquescent substance in the range of from about 0.5 percent to about 20 percent by weight.

71. A poultry litter composition comprising at least one poultry litter material and an effective dust generation inhibiting amount of a propionate free liquid composition comprising an effective moisture migration inhibiting amount of at least one deliquescent substance.

72. A poultry litter composition according to claim 71, wherein said deliquescent substance comprises at least one deliquescent substance from the group consisting of magnesium chloride, calcium chloride, manganese chloride, ferric chloride and zinc chloride.

73. A poultry litter composition according to claim 71, wherein said deliquescent substance comprises at least one deliquescent substance selected from the group consisting of ammonium citrate, calcium chlorate, calcium chloride, calcium iodide, calcium nitrite, cobaltous ammonium chloride, cobaltous iodide, cupric chlorate, cupric nitrate, ferric chloride, ferric lactate, ferric nitrate, ferrous iodide, magnesium ammonium chloride, magnesium chlorate, magnesium chloride, magnesium iodide, magnesium nitrate, magnesium potassium chloride, manganese chloride, manganese oxide, manganese sulphate, phosphoric acid, phosphorus oxide, potassium acetate, potassium carbonate, potassium iodide, potassium phosphate, sodium bisulphate, stannic sulphate, and zinc chloride.

74. A poultry litter composition according to claim 71, wherein said amount of said liquid composition is insufficient to cause said poultry litter to take on from the air any substantial amount of additional moisture than it contained upon application of said liquid composition to said poultry litter material.

75. A poultry litter composition according to claim 71, wherein said poultry litter material contains at least about 36 grams of said deliquescent substance per ton of said poultry litter material.

76. A poultry litter composition according to claim 71, wherein said poultry litter material contains not more than about 100 grams of said deliquescent substance per ton of said poultry litter material.

77. A poultry litter composition according to claim 71, wherein said poultry litter material contains an amount of said deliquescent substance in the range of from about 36 grams to about 72 grams per ton of said poultry litter material.

78. A poultry litter composition according to claim 71, wherein said liquid composition contains at least about 0.5 percent by weight of said deliquescent substance.

79. A poultry litter composition according to claim 71, wherein said liquid composition contains not more than about 20 percent by weight of said deliquescent substance.

80. A poultry litter composition according to claim 71, wherein said liquid composition contains an amount of said deliquescent substance in the range of from about 0.5 percent to about 20 percent by weight.

* * * * *